US00PP24147P2

(12) United States Plant Patent
Misato

(10) Patent No.: US PP24,147 P2
(45) Date of Patent: Jan. 7, 2014

(54) ***VERBENA* PLANT NAMED 'SUNTAPILILA'**

(50) Latin Name: *Verbena×hybrida*
Varietal Denomination: Suntapilila

(75) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 13/506,827

(22) Filed: May 17, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Kent L Bell
(74) *Attorney, Agent, or Firm* — C. A. Whealy

(57) ABSTRACT

A new and distinct cultivar of *Verbena* plant named 'Suntapilila', characterized by its upright and outwardly spreading plant habit; vigorous growth habit; freely branching habit; early and freely flowering habit; and light purple violet-colored flowers that are held above and beyond the foliar plane.

1 Drawing Sheet

Botanical designation: *Verbena×hybrida.*
Cultivar denomination: 'SUNTAPILILA'.

BACKGROUND OF THE INVENTION

The present invention relates to a new and distinct cultivar of *Verbena* plant, botanically known as *Verbena×hybrida* and hereinafter referred to by the name 'Suntapilila'.

The new *Verbena* plant is a product of a planned breeding program conducted by the Inventor in Higashiomi, Shiga, Japan. The objective of the breeding program is to create new freely branching *Verbena* plants with upright and outwardly spreading plant habit and attractive flower coloration.

The new *Verbena* plant originated from a cross-pollination made by the Inventor in November, 2004 in Higashiomi, Shiga, Japan of a proprietary selection of *Verbena×hybrida* identified as code number VW415, not patented, as the female, or seed, parent with a proprietary selection of *Verbena×hybrida* identified as code number VW203, not patented, as the male, or pollen, parent. The new *Verbena* plant was discovered and selected by the Inventor as a single flowering plant from within the progeny of the stated cross-pollination in a controlled greenhouse environment in Higashiomi, Shiga, Japan in October, 2005.

Asexual reproduction of the new *Verbena* plant by cuttings in a controlled greenhouse environment in Higashiomi, Shiga, Japan since October, 2005 has shown that the unique features of this new *Verbena* plant are stable and reproduced true to type in successive generations.

SUMMARY OF THE INVENTION

Plants of the new *Verbena* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Suntapilila'. These characteristics in combination distinguish 'Suntapilila' as a new and distinct *Verbena* plant:

1. Upright and outwardly spreading plant habit.
2. Vigorous growth habit.
3. Freely branching habit.
4. Early and freely flowering habit.
5. Light purple violet-colored flowers that are held above and beyond the foliar plane.

Plants of the new *Verbena* can be compared to plants of the female parent selection. Plants of the new *Verbena* differ primarily from plants of the female parent selection in plant habit as plants of the new *Verbena* are more outwardly spreading than and not as upright as plants of the female parent selection.

Plants of the new *Verbena* can be compared to plants of the male parent selection. Plants of the new *Verbena* differ primarily from plants of the male parent selection in flower color as plants of the male parent selection have violet-colored flowers. In addition, plants of the new *Verbena* are not as trailing as plants of the male parent selection.

Plants of the new *Verbena* can be compared to plants of the *Verbena×hybrida* 'Suntapiripi', disclosed in U.S. Plant Pat. No. 23,297. In side-by-side comparisons conducted in Higashiomi, Shiga, Japan, plants of the new *Verbena* differed primarily from plants of 'Suntapiripi' in the following characteristics:

1. Plants of the new *Verbena* were more upright than and not as trailing as plants of 'Suntapiripi'.
2. Plants of the new *Verbena* were taller than plants of 'Suntapiripi'.
3. Plants of the new *Verbena* had longer internodes than plants of 'Suntapiripi'.
4. Plants of the new *Verbena* had longer and narrower leaves than plants of 'Suntapiripi'.
5. Flowers of plants of the new *Verbena* were smaller than flowers of plants of 'Suntapiripi'.
6. Flowers of plants of the new *Verbena* were darker and more violet in color than flowers of plants of 'Suntapiripi'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the colors of the new *Verbena* plant.

The photograph at the top of the sheet comprises a side perspective view of a typical flowering plant of 'Suntapilila' grown in a container.

The photograph at the bottom of the sheet is a close-up view of a typical inflorescence of 'Suntapilila'.

DETAILED BOTANICAL DESCRIPTION

The aforementioned photographs and following observations and measurements describe plants grown during the late spring in 15-cm containers in an outdoor nursery in Higashiomi, Shiga, Japan under cultural practices typical of commercial *Verbena* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Verbena×hybrida* 'Suntapilila'.

Parentage:

*Female, or seed, parent.*—Proprietary selection of *Verbena×hybrida* identified as code number VW415, not patented.

*Male, or pollen, parent.*—Proprietary selection of *Verbena×hybrida* identified as code number VW203, not patented.

Propagation:

*Type.*—By cuttings.

*Time to initiate roots.*—About 10 to 14 days at 20° C. to 25° C.

*Time to produce a rooted young plant.*—About four weeks at 20° C. to 25° C.

*Root description.*—Fibrous; white in color.

*Rooting habit.*—Freely branching.

Plant description:

*Plant and growth habit.*—Upright and outwardly spreading plant habit; freely branching habit with numerous lateral branches developing per plant, pinching enhances lateral branch development; vigorous growth habit.

*Plant height.*—About 20 cm.

*Plant diameter.*—About 56.5 cm.

Lateral branch description:

*Length.*—About 29.6 cm.

*Diameter.*—About 1.4 mm.

*Internode length.*—About 3.3 cm.

*Strength.*—Strong; flexible.

*Texture.*—Pubescent, strigose.

*Color.*—Close to 143B to 143C; at the peduncle, tinted with close to 59C.

Foliage description:

*Arrangement.*—Opposite, simple.

*Length.*—About 3.7 cm.

*Width.*—About 2.6 cm.

*Shape.*—Pinnately parted.

*Apex.*—Acute.

*Base.*—Cuneate.

*Margin.*—Pinnately cleft.

*Texture, upper and lower surfaces.*—Pubescent, coarse.

*Venation pattern.*—Pinnate; reticulate.

*Color.*—Developing leaves, upper surface: Close to 137C. Developing leaves, lower surface: Close to 138B. Fully expanded leaves, upper surface: Close to 137B; venation, close to 144B. Fully expanded leaves, lower surface: Close to 138B; venation, close to 144B.

*Petiole.*—Length: About 7 mm. Diameter: About 1.5 mm. Texture, upper and lower surfaces: Pubescent. Color, upper and lower surfaces: Close to 143B with longitudinal lines, close to 144C.

Flower description:

*Flower arrangement and habit.*—Salverform flowers arranged in hemispherical terminal racemes; flowers face mostly upright and outwardly; flowers sessile; freely flowering habit with about 17 flowers per inflorescence and numerous inflorescences developing per plant.

*Natural flowering season.*—Plants flower continuously from spring to late autumn in Japan; plants begin flowering about four weeks after planting.

*Flower longevity.*—Flowers last about one week on the plant; flowers not persistent.

*Fragrance.*—None detected.

*Inflorescence height.*—About 2.5 cm.

*Inflorescence diameter.*—About 4 cm.

*Flowers.*—Appearance: Flared trumpet, corolla fused, five-parted. Diameter: About 1.3 cm. Depth (height): About 1.9 cm. Tube length: About 1.3 cm. Tube diameter: About 1.1 mm.

*Flower buds.*—Length: About 1.1 cm. Diameter: About 1.5 mm. Shape: Clavate. Color: Close to N80A.

*Corolla.*—Arrangement: Single whorl of five fused petals. Petal length: About 6.1 mm. Petal width: About 5.4 mm. Petal lobe shape: Cordate. Petal lobe apex: Cordate. Petal lobe margin: Entire. Petal texture, upper and lower surfaces: Smooth, glabrous. Color: Petal, when opening and fully opened, upper surface: Close to N82A. Petal, when opening and fully opened, lower surface: Close to N82C. Throat: Close to 76B; proximally, close to 4D with longitudinal lines, close to 76B. Tube: Close to 4D with longitudinal lines, close to 76B.

*Calyx.*—Arrangement: One single narrow calyx tube per flower with five fused sepals. Sepal length: About 1.2 mm. Sepal width: About 0.2 mm. Sepal shape: Triangular. Sepal apex: Acute. Sepal margin: Entire. Sepal texture, upper and lower surfaces: Pubescent. Sepal color: When developing, upper surface: Close to 149B. When developing, lower surface: Close to 143C. Fully developed, upper surface: Close to 143A tinged with close to 59C. Fully developed, lower surface: Close to 143C.

*Peduncles.*—Length: About 3.2 cm. Diameter: About 1.2 mm. Strength: Strong; flexible. Texture: Pubescent, strigose. Color: Close to 146B.

*Reproductive organs.*—Stamens: Quantity and arrangement: Four per flower, adnate to corolla tube. Anther shape: Ellipsoidal. Anther size: About 0.9 mm by 1.1 mm. Anther color: Close to 1C. Pollen amount: None observed. Pistils: Quantity: One per flower. Pistil length: About 1.2 cm. Stigma shape: Bi-parted. Stigma color: Close to 145C. Style color: Close to 145D. Ovary color: Close to N144C. Fruits and seeds: Fruit and seed development have not been observed on plants of the new *Verbena*.

Temperature tolerance: Plants of the new *Verbena* have been observed to tolerate temperatures from about 0° C. to about 35° C.

Pathogen & pest resistance: Plants of the new *Verbena* have not been observed to be resistant to pathogens and pests common to *Verbena* plants.

It is claimed:

1. A new and distinct *Verbena* plant named 'Suntapilila' as illustrated and described.

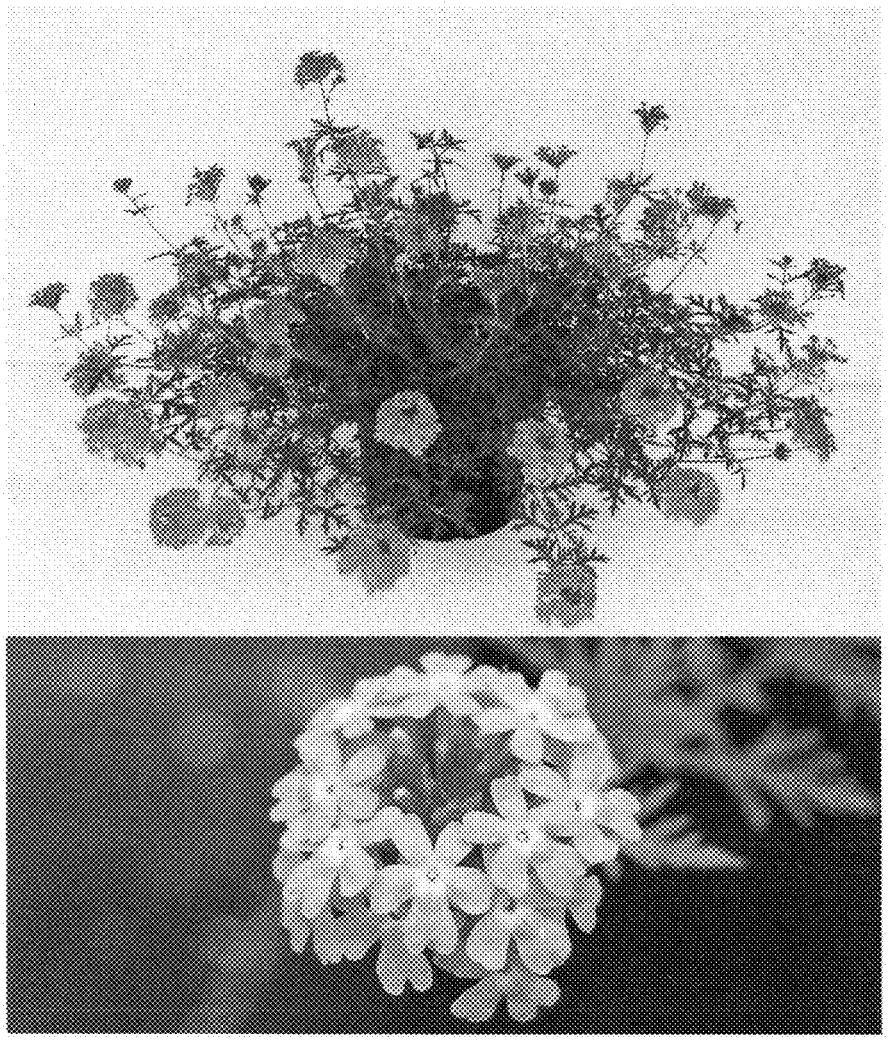

* * * * *